United States Patent [19]

Bakassian et al.

[11] 4,001,178
[45] Jan. 4, 1977

[54] ORGANO-TIN MERCAPTIDES WITH POLYSULPHANEDIYL GROUPS

[75] Inventors: Georges Bakassian, Les Lyon; Michel Gay, Lyon, both of France

[73] Assignee: Rhone-Poulenc, Paris, France

[22] Filed: May 10, 1974

[21] Appl. No.: 468,997

[30] Foreign Application Priority Data

May 14, 1973 France .......................... 73.17326

[52] U.S. Cl. .................. 260/45.75 S; 260/429.7
[51] Int. Cl.² ...................................... C08K 5/58
[58] Field of Search ............. 260/429.7, 45.75 S

[56] References Cited

UNITED STATES PATENTS 2,752,325  6/1956  Leistner et al. ............... 260/429.7
3,819,673  6/1974  Sagi et al. ..................... 260/429.7

OTHER PUBLICATIONS

Reid, Organic Chemistry of Bivalent Sulfur, vol. III, p. 399 (1958).
Reid, vol. II, pp. 211–219.
Reid, vol. I, pp. 118, 120.

*Primary Examiner*—Helen M. S. Sneed
*Attorney, Agent, or Firm*—Bacon & Thomas

[57] ABSTRACT

Organo-tin mercaptides containing polysulphanediyl groups are produced from a mercaptocarboxylic acid, a diorgano-tin derivative and a diol with a polysulphanediyl and, optionally, monoalcohols and monoorgano-tin derivative. Such mercaptides give vinyl chloride polymers improved resistance to yellowing.

7 Claims, No Drawings

ORGANO-TIN MERCAPTIDES WITH POLYSULPHANEDIYL GROUPS

The present invention relates to organo-tin mercaptides which contain polysulphanediyl radicals.

It is known from, for example, French Pat. Nos. 1,055,906, 1,085,807 and 1,138,451 that diorgano-tin mercaptides are good stabilisers for chlorinated vinyl resins, especially polyvinyl chloride. It has been proposed to use, in particular, saturated mercaptides such as dibutyl- or dioctyl-tin bis-(isooctylmercaptoacetate) since these are considered to be the most effective stabilisers. However, these compounds are not wholly satisfactory. For example, they do not prevent the appearance of a yellow colouration during the manufacture of transparent thin-walled articles by extrusion at a high temperature. It is known that such a technique can be carried out to a worthwhile extent only if the chlorinated vinyl resin compositions are heated for short periods, for example for 2 to 5 minutes, to temperatures of 180° to 230° C.

New organo-tin mercaptides have now been found, according to the present invention, which make it possible, in particular, to reduce considerably the yellowing effect observed during the extrusion, at a high temperature, of transparent thin-walled articles. These organo-tin mercaptides contain polysulphanediyl groups and consist essentially of groups of the formula (I):

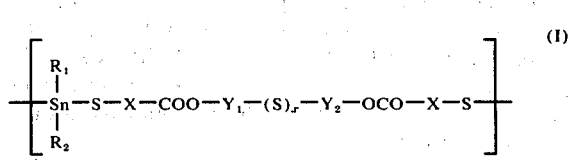

and are produced by a process according to this invention which comprises:

a. in a first step, reacting a mercaptocarboxylic acid of the formula:

$$HS - X - COOH$$

with a mixture of hydroxylic compounds of the formula:

$$HO - Y_1 - (S)_x - Y_2 - OH,$$

$$HO - Y' - OH \text{ and}$$

$$ROH,$$

in which X represents a straight or branched alkylene group with 1 to 4 carbon atoms or a phenylene group; x represents an integer from 2 to 6; $Y_1$ and $Y_2$, which may be identical or different, each represents a divalent hydrocarbon radical, the free valencies of which are not attached to aromatic carbon atoms, namely a straight or branched alkylene group with at most 6 carbon atoms, which is optionally substituted by one or more phenyl or alkylphenyl radicals, the alkyl substituent of the phenyl radical having 1 to 6 carbon atoms, a cycloalkylene group with 5 or 6 carbon atoms in the ring, or a group of the formula - $Z_1$ - S - $Z_2$ - in which the divalent radicals $Z_1$ and $Z_2$, which may be identical or different, each represents a straight or branched alkylene radical with 1 to 6 carbon atoms; Y' represents a divalent hydrocarbon radical which may be a straight or branched aliphatic radical with at most 10 carbon atoms, or a cycloaliphatic radical with 5 or 6 carbon atoms in the ring, it being possible for the radical Y' optionally to possess one ethylenic or acetylenic unsaturated bond or to contain two ethylenic and/or acetylenic unsaturated bonds; R represents a straight or branched alkyl or alkenyl radical with at most 8 carbon atoms, a cycloalkyl or cycloalkenyl radical with 5 or 6 carbon atoms in the ring, or a phenylalkyl group in which the alkyl substituent contains 1 to 4 carbon atoms, and $R_1$ and $R_2$, which may be identical or different, each represents a straight or branched alkyl group with 1 to 10 carbon atoms.

Such that if the molar ratio of HS - X - COOH, HO - $Y_1$ - (S)$_x$ - $Y_2$ - OH, OH - Y' - OH and ROH is respectively, $x_1$:$y_1$:$y_2$:$y_3$

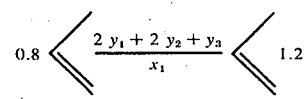

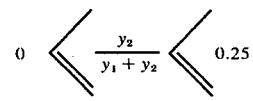

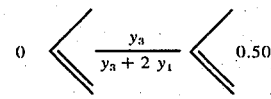

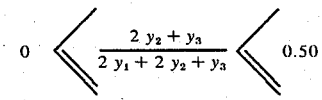

b. in a second step, reacting the resulting product with a mixture consisting of: $z_1$ mols of a diorgano-tin derivative which is either a dialkyl-tin oxide of formula: $R_1R_2SnO$ or a dichlorodialkylstannane of formula: $R_1R_2SnCl_2$; and $z_2$ mol of a monoorgano-tin derivative which is either a stannoic acid monomer or polymer of formula $(R_1SnO_{1.5})_n$ or $R_1SnCl_3$, $R_1Sn(OH)Cl_2$ or $R_1Sn(OH)_2Cl$, in which n is a number from 2 to 1,000, and preferably from 2 to 100, such that:

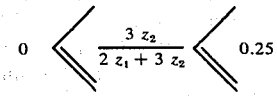

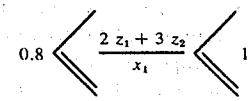

The organo-tin mercaptides produced according to the process of this invention have a complex structure and can contain, in particular, the following groups:

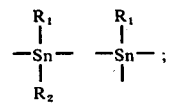

$$- S - X - COO - Y_1 - (S)_x - Y_2 - OCO - X - S -$$
$$- S - X - COO - Y' - OCO - X - S - \text{ and}$$

- S - X - COOR

Each mercaptide molecule generally contains 1 to 5

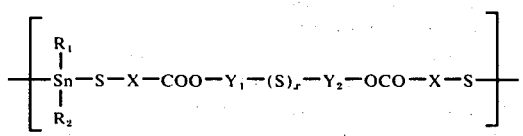

groups, forming monomeric, dimeric or oligomeric compounds. By way of illustration, the monomeric and dimeric forms may be:

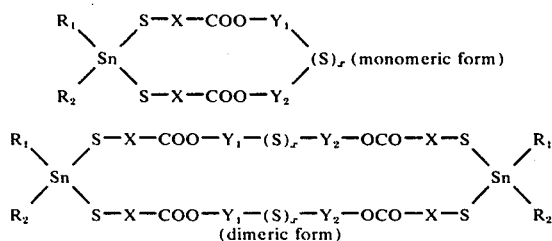

In the process of this invention, it is essential that a diol with a polysulphanediyl group HO - $Y_1$ - $(S)_x$ - $Y_2$ - OH (hereinafter referred to as the "sulphur-containing diol") and a diorgano-tin compound are reacted. The use of one of the following reagents, namely a saturated or unsaturated diol, a saturated or unsaturated monoalcohol and a monoorgano-tin derivative, is optional. It is thus possible to define various processes for the manufacture of the mercaptides which are simpler, depending on whether either the sulphur-containing diol or the diorgano-tin derivative is partially replaced by the optional reactants.

The most complex process is that in which all the different reactants which are possible are used. As is apparent from the conditions set out above, the replacement of a part of the sulphur-containing diol is such that the proportion of hydroxyl groups provided by the diol HO - Y' - OH and/or the monoalcohol is at most equal to 50% of the sum total of the hydroxyl groups present in the sulphur-containing diol and the diol HO - Y' - OH and/or the monoalcohol. Furthermore, the tin-mercaptoester group bonds (joined via the sulphur atom) provided by the mono-organo-tin derivative make up at most 25% of all the tin-mercaptoester group bonds formed from the diorgano-tin derivative and from the monoorgano-tin derivative.

The product which results from the first step of the process is unstable and changes readily into a resinous substance. It is thus advisable not to attempt to isolate it and to use it rapidly, as it is, for the second step. The intermediate product comprises, in particular, the α,ω-dimercapto-diester of the formula:

HS - X - COO - $Y_1$ - $(S)_x$ - $Y_2$ - OCO - X - SH sometimes together with a small proportion of biproducts of the formula:

HOOC - X - S - $Y_1$ - $(S)_x$ - $Y_2$ - S - X - COOH and
HOOC - X - S - $Y_1$ - $(S)_x$ - $Y_2$ - OCO - X - SH It is recommended that the process according to this invention be carried out in a solvent which is not miscible with water such as aliphatic, cycloaliphatic or aromatic hydrocarbons, for example, hexane, cyclohexane, petroleum ether, methylcyclohexane, benzene and toluene. The water formed during the reaction is advantageously removed by azeotropic distillation. In order to promote the esterification reaction in the first step, it is possible to add a known esterification catalyst, for example p-toluenesulphonic acid or sulphuric acid. The conversion to the tin mercaptide is advantageously carried out by employing a dialkyl-tin oxide. If a dichloro-dialkyl-stannane is used, it is preferable to introduce simultaneously an agent such as ammonia or an amine, which will neutralise the hydrochloric acid liberated.

Amongst the diorgano-tin derivatives which may be used, there may be mentioned by way of illustration: dimethyl-tin oxide, dibutyl-tin oxide and dioctyl-tin oxide, dichloro-dimethylstannane, dichloro-dibutylstannane and dichloro-dioctyl stannane. Amongst the monoorgano-tin derivatives, there may be mentioned butyl-stannoic acid and octyl-stannoic acid, in dimeric or polymeric form.

The sulphur-containing diols can be produced readily either by controlled oxidation of mercaptoalcohol or by reacting a halogenated alcohol with an alkali metal or ammonium sulphide or polysulphide. Such methods are described in for example, "Organic Chemistry of Bivalent Sulphur", Volume 1, pages 120–124 and Volume 2, pages 212–213, 1958, E. REID. For example, if a mercaptoalcohol of formula HO - $Y_1$ - SH is oxidised by means of oxygen in the presence of an iron or copper derivative, access is gained to disulphides of the general formula HO - $Y_1$ - S - S - $Y_1$ - OH. Using this process, it is also possible to oxidise a mixture of mercaptoalcohols in order to produce asymmetrical dihydroxydisulphides.

The reaction of halogenated alcohols of formula HO - $Y_1$ - Cl with an alkali metal or ammonium polysulphide leads to dihydroxy-polysulphides of formula HO - $Y_1$ - $(S)_x$ - $Y_1$ - OH. The latter consist of a mixture of polysulphides, in which $x$ can have any value from 2 to 6.

Amongst the sulphur-containing diols, there may be mentioned by way of illustration, the diols containing disulphide groups, of the formula

HO-CH$_2$-CH$_2$-S-S-CH$_2$-CH$_2$-OH

HO-CH$_2$-CH$_2$-S-CH$_2$-CH$_2$-S-S-CH$_2$-CH$_2$-S-CH$_2$-CH$_2$-OH

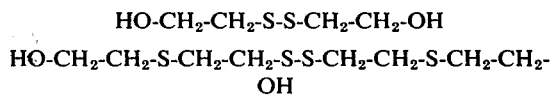

HO-CH$_2$-CH$_2$-CH$_2$-S-S-CH$_2$-CH$_2$-CH$_2$-OH

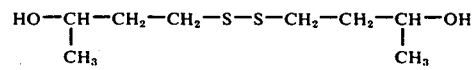

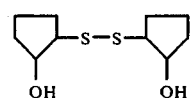

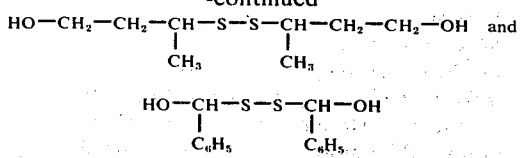

It is also possible to use sulphur-containing diols with a polysulphanediyl group, the formulae of which can be derived from the formulae given above by replacing the disulphide group by a polysulphide group containing 2 to 6 sulphur atoms. These diols with a polysulphanediyl group generally consist of a mixture of varying proportions of sulphur-containing diols possessing a di-, tri-, tetra-, penta- or hexa-sulphide chain.

Typical mercaptocarboxylic acids, which may be used include, thioglycollic acid, β-mercaptopropionic acid, γ-mercaptobutyric acid, δ-mercaptovaleric acid, thiolactic acid, thiosalicylic acid, α- and β-mercaptobutyric acids and β- and γ-mercaptovaleric acids.

Amongst the hydrocarbon diols of formula HO - Y' - OH, there may be mentioned, for example, the saturated diols, propane-1,3-diol, butane-1,4-diol, pentane-1,5-diol, hexane-1,6-diol, octane-1,8-diol, butane-3,4-diol, pentane-1,4-diol, pinacol and 3-methylheptane-4,5-diol; unsaturated diols, but-2-ene-1,4-diol, pent-2-ene-1,5-diol, hexene-1,6-diol, octene-1,8-diol, but-1-ene-3,4-diol, pent-1-ene-3,4-diol, pent-2-ene-1,4-diol, hex-2-ene-1,5-diol, hept-3-ene-6,7-diol, oct-4-ene-3,6-diol, but-2-yne-1,4-diol, pent-2-yne-1,4-diol, hex-3-yne-2,5-diol, hexa-1,5-diene-3,4-diol, oct-4-yne-3,6-diol, octa-2,6-diene-4,5-diol and 3-methyl-hepta-2,6-diene-4,5-diol.

Amongst the saturated or unsaturated monoalcohols, there may be mentioned, purely by way of illustration: isobutanol, n-butanol, isooctanol, octanol, cyclopentanol, cyclohexanol and phenylethyl alcohol.

According to a variant, it is also possible to use a mixture of sulphur-containing diols, diols HO - Y' - OH, saturated or unsaturated monoalcohols and diorgano-tin or monoorgano-tin derivatives, provided that the specified proportions defined above are respected.

The mercaptides which consist essentially of groups of formula (I) can be used, after removing solvent, if any, to stabilise halogenated vinyl resins. They are generally introduced into the resin in an amount from 0.2 to 3% by weight relative to the resin. By "halogenated vinyl resins", as used herein, are meant, in accordance with the terminology which is well known to those skilled in the art, polyvinyl chloride and vinyl chloride copolymers in which the part originating from vinyl chloride predominates. Amongst the compounds which are suitable for copolymerisation with vinyl chloride, there may be mentioned: vinyl esters such as vinyl acetate, and vinyl butyrate, vinyl bromide, vinyl fluoride, vinyl ethers such as vinyl ethyl ether, acrylic acid and its derivatives such as ethyl acrylate, ethyl methacrylate, acrylonitrile and acrylamide, allyl compounds such as allyl chloride and allyl acetate, and ethylenic compounds such as ethylene, propylene and butadiene.

The mercaptides according to the present invention retard the yellowing effect more than their saturated homologues. These mercaptides are thus particularly suitable for producing thin films or transparent articles by extrusion or calendering techniques.

The following Examples further illustrate the invention.

EXAMPLE 1

60 g. of 2-mercapto-ethanol and 300 ml of benzene are introduced into a flask and 43 g of 110 volumes strength hydrogen peroxide (30% $H_2O_2$) are run in over the course of 2 hours whilst keeping the flask at about 20° C. When the running in is complete, 300 ml of benzene are added and the water is removed by azeotropic distillation. 75 g. of thioglycollic acid and 1 g of p-toluenesulphonic acid are added to the dithiodiglycol thus produced, in benzene solution, and the mixture is heated under reflux (77° – 82° C) for 1 hour 30 minutes, removing the water formed during the reaction by azeotropic distillation. The mixture is cooled and 94.5 g. of dibutyl-tin oxide are introduced and the whole is heated under reflux for 2 hours, removing the water formed by the reaction by azeotropic distillation. After removing the benzene, 209 g. of organo-tin mercaptide, which consists essentially of groups of the formula

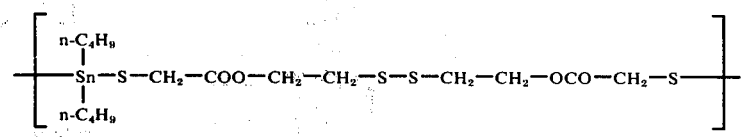

are obtained. This structure was identified, in particular, by infra-red analysis.

EXAMPLE 2

19.3 g. of dithio-diglycol, 26.5 g. of mercaptopropionic acid, 1 g. of p-toluenesulphonic acid and 300 ml of benzene are introduced into a flask. The mixture is heated under reflux (82° C) for 3 hours whilst the water formed during the reaction is removed by azeotropic distillation. 45.2 g. of di-(n-octyl)-tin oxide are then added and the mixture is heated under reflux until all the water formed by the reaction has been removed by azeotropic distillation. After distilling the benzene, 84 g. of organo-tin mercaptide, consisting essentially of groups of the formula:

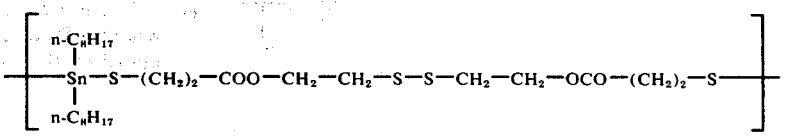

are obtained.

EXAMPLE 3

Various samples based on polyvinyl chloride resin having the following composition are prepared:

| | |
|---|---|
| commercial polyvinyl chloride, sold under the trademark LUCOVYL BB 800 | 100 g. |
| styrene/butadiene/methyl methacrylate terpolymer, used as an agent for improving impact strength, | 10 g. |
| ester of 1,3-(butylene glycol) and oxidised lignite wax sold commercially under the brand-name "wax E" | 1 g. |
| stabiliser (organo-tin mercaptide) | 1 g. |

Each mixture is melted in a two roll mixer turning at a rate of 15 revolutions/minute and heated to 180° C (temperature maintained to within about 2° C). These samples are removed, the first after being worked for 5 minutes on the calenders and the rest at 3 minute intervals thereafter. The yellow indices according to the Gardner scale are noted using a Lovibond comparison disc. By way of comparison, the Table which follows also gives the results obtained with the organo-tin mercaptide which is a homologue of that described in Example 1 but which differs therefrom by the absence of a disulphanediyl group, i.e. it consists essentially of the following groups:

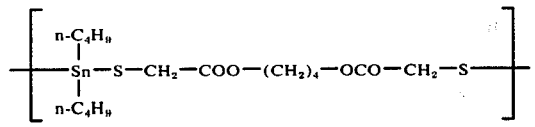

| | Stabilised PVC resin | |
|---|---|---|
| Duration of heating at 180° in minutes | Stabiliser of Example 1 Gardner index | Homologous stabiliser without a disulphane-diyl group |
| 5 | 0 | 0 |
| 8 | 0 | 1 |
| 11 | 0 | 2 |
| 14 | 0 | 2 |
| 17 | 0 | 2 |
| 20 | 1 | 3 |

We claim:

1. An organo-tin mercaptide consisting essentially of groups of the formula:

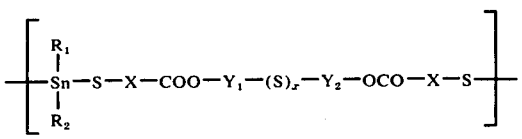

in which X represents a straight or branched chain alkylene group with up to 4 carbon atoms or a phenylene group;

x represents an integer from 2 to 6;

$Y_1$ and $Y_2$, which may be identical or different each represents a straight or branched chain alkylene group with at most 6 carbon atoms, and $R_1$ and $R_2$, which may be identical or different, each represents a straight or branched chain alkyl group with 1 to 10 carbon atoms.

2. A halogenated vinyl resin containing 0.2 to 3% by weight of an organo-tin mercaptide consisting essentially of groups of the formula:

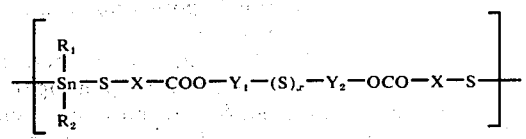

in which X represents a straight or branched chain alkylene group with up to 4 carbon atoms or a phenylene group;

x represents an integer from 2 to 6;

$Y_1$ and $Y_2$, which may be identical or different each represents a straight or branched chain alkylene group with at most 6 carbon atoms, and $R_1$ and $R_2$, which may be identical or different, each represents a straight or branched chain alkyl group with 1 to 10 carbon atoms.

3. Polyvinyl chloride containing 0.2 to 3% by weight of an organo-tin mercaptide consisting essentially of groups of the formula:

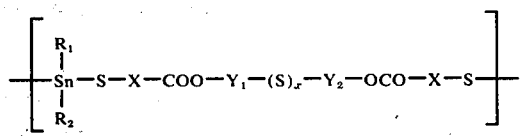

in which X represents a straight or branched chain alkylene group with up to 4 carbon atoms or a phenylene group;

x represents an integer from 2 to 6;

$Y_1$ and $Y_2$, which may be identical or different each represents a straight or branched chain alkylene group with at most 6 carbon atoms, and $R_1$ and $R_2$, which may be identical or different, each represents a straight or branched chain alkyl group with 1 to 10 carbon atoms.

4. The organo-tin mercaptide as defined by claim 1, wherein x is 2.

5. The organo-tin mercaptide as defined by claim 4, wherein $Y_1$ and $Y_2$ are ethylene.

6. The organo-tin mercaptide as defined by claim 1, wherein $R_1$ and $R_2$ are selected from the group consisting of methyl, butyl and octyl.

7. The organo-tin mercaptide as defined by claim 4, wherein $R_1$ and $R_2$ are selected from the group consisting of methyl, butyl and octyl.

* * * * *